(12) United States Patent
Jang et al.

(10) Patent No.: US 11,204,276 B2
(45) Date of Patent: Dec. 21, 2021

(54) APPARATUS AND METHOD FOR ANALYZING COMPONENT OF OBJECT, AND IMAGE SENSOR

(71) Applicant: SAMSUNG ELECTRONICS CO., LTD., Suwon-si (KR)

(72) Inventors: Hyeong Seok Jang, Seoul (KR); Hyun Seok Moon, Seoul (KR); Jae Wook Shim, Yongin-si (KR); Kun Sun Eom, Yongin-si (KR); Myoung Hoon Jung, Bucheon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 16/923,608

(22) Filed: Jul. 8, 2020

(65) Prior Publication Data

US 2020/0340917 A1    Oct. 29, 2020

Related U.S. Application Data

(62) Division of application No. 16/253,450, filed on Jan. 22, 2019, now Pat. No. 10,739,195.

(30) Foreign Application Priority Data

Aug. 1, 2018   (KR) .................. 10-2018-0089785

(51) Int. Cl.
*G01J 3/10* (2006.01)
*A61B 5/00* (2006.01)
(Continued)

(52) U.S. Cl.
CPC .............. *G01J 3/10* (2013.01); *A61B 5/0075* (2013.01); *G01J 3/0205* (2013.01);
(Continued)

(58) Field of Classification Search
CPC .......... G01J 3/10; G01J 3/0205; G01J 3/0264; G01J 3/4412; A61B 5/0075;
(Continued)

(56) References Cited

U.S. PATENT DOCUMENTS

| | | | |
|---|---|---|---|
| 5,818,583 A | 10/1998 | Sevick-Muraca et al. | |
| 6,381,018 B1 | 4/2002 | Bigio et al. | |

(Continued)

FOREIGN PATENT DOCUMENTS

| | | | |
|---|---|---|---|
| JP | 2017-136183 A | 8/2017 | |
| KR | 10-2010-0083288 A | 7/2010 | |
| KR | 10-2018-0010945 A | 1/2018 | |

OTHER PUBLICATIONS

Hu et al., "Noncontact and Wide-Field Characterization of the Absorption and Scattering Properties of Apple Fruit Using Spatial-Frequency Domain Imaging", Scientific Reports, 11 total pages.

(Continued)

*Primary Examiner* — Tri T Ton
(74) *Attorney, Agent, or Firm* — Sughrue Mion, PLLC

(57) ABSTRACT

A method and an apparatus for analyzing a component of an object are provided. The apparatus includes an image sensor including an optical module, and the optical module includes a light source configured to emit a source light, a first detector configured to detect a first light that is scattered or reflected from the object on which the emitted source light is incident, and a second detector configured to detect a second light that is emitted by the light source but is not incident on the object. The apparatus further includes a processor configured to calculate a scattering coefficient and an absorption coefficient, based on the detected first light and the detected second light, and analyze the component of the object, based on the calculated scattering coefficient and the calculated absorption coefficient.

7 Claims, 17 Drawing Sheets

(51) Int. Cl.
   *G01J 3/02*     (2006.01)
   *G01J 3/44*     (2006.01)
   *G01N 21/47*    (2006.01)
   *G01N 21/59*    (2006.01)

(52) U.S. Cl.
   CPC ........... *G01J 3/0264* (2013.01); *G01J 3/4412* (2013.01); *G01N 21/47* (2013.01); *G01N 21/4795* (2013.01); *G01N 21/59* (2013.01); *A61B 2562/04* (2013.01); *G01N 2201/062* (2013.01); *G01N 2201/0635* (2013.01); *G01N 2201/0636* (2013.01); *G01N 2201/06113* (2013.01); *G01N 2201/08* (2013.01)

(58) Field of Classification Search
   CPC ............ A61B 2562/04; A61B 5/14532; A61B 5/1455; A61B 5/1495; G01N 21/47; G01N 21/474; G01N 21/4785; G01N 21/4795; G01N 21/49; G01N 21/59; G01N 2201/0221; G01N 2201/06113; G01N 2201/062; G01N 2201/0635; G01N 2201/0636; G01N 2201/08; G01N 2021/1734; G01N 2021/1765; G01N 2021/3133; G01N 21/31; G01N 21/55; G01N 21/84; G01N 33/50
   USPC ................................................. 356/432–448
   See application file for complete search history.

(56) References Cited

U.S. PATENT DOCUMENTS

| | | |
|---|---|---|
| 6,635,491 B1 | 10/2003 | Khalil et al. |
| 7,228,166 B1 | 6/2007 | Kawasaki et al. |
| 10,126,111 B2 | 11/2018 | Levitz |
| 2006/0033928 A1 | 2/2006 | Chou et al. |
| 2008/0101657 A1 | 5/2008 | Durkin et al. |
| 2015/0201841 A1 | 7/2015 | Ishikawa et al. |
| 2016/0206206 A1 | 7/2016 | Avila et al. |
| 2016/0206251 A1 | 7/2016 | Kwon et al. |
| 2016/0309068 A1 | 10/2016 | Nadeau et al. |
| 2017/0108433 A1 | 4/2017 | Helfmann et al. |

OTHER PUBLICATIONS

Communication dated Nov. 26, 2019, issued by the European Patent Office in corresponding European Application No. 19189507.7.

APPARATUS AND METHOD FOR ANALYZING COMPONENT OF OBJECT, AND IMAGE SENSOR

CROSS-REFERENCE TO RELATED APPLICATION

This application is a divisional application of U.S. application Ser. No. 16/253,450 filed Jan. 22, 2019, which claims priority from Korean Patent Application No. 10-2018-0089785, filed on Aug. 1, 2018, in the Korean Intellectual Property Office, the entire disclosures of which are herein incorporated by reference for all purposes.

BACKGROUND

1. Field

Apparatuses and methods consistent with embodiments relate to analyzing components of an object, and an image sensor mounted in the apparatus for analyzing components of an object.

2. Description of the Related Art

Absorbance may be used to analyze samples in various applications such as environment monitoring, food inspection, medical diagnosis, and the like. Research has been conducted on a method of continuously measuring skin absorbance with a small spectrometer to analyze various components of an object based on the measurements. A measurement result of bio-signals may be changed due to skin inhomogeneity. In the case in which bio-signals are measured from skin, two-dimensional measurement may be performed to reduce a measurement error caused by the inhomogeneity. A general measurement system, which uses an image sensor based on spatial frequency domain imaging, may not be suitable for use in wearable device because of its large size. Further, to measure absorbance accurately, a reference may have to be measured every time the absorbance is measured, such that it is difficult to monitor bio-signals continuously.

SUMMARY

According to an aspect of an embodiment, there is provided an image sensor including an optical module, and the optical module includes a light source configured to emit a source light, a first detector configured to detect a first light that is scattered or reflected from the object on which the emitted source light is incident, and a second detector configured to detect a second light that is emitted by the light source but is not incident on the object. The apparatus further includes a processor configured to calculate a scattering coefficient and an absorption coefficient, based on the detected first light and the detected second light, and analyze the component of the object, based on the calculated scattering coefficient and the calculated absorption coefficient.

The image sensor may further include a substrate on which the optical module is disposed at each of nodes to form a network structure.

A first portion of the emitted source light may be emitted from a first surface of the light source, may be incident on the object, may be scattered or reflected from the object, may pass through a first hole disposed through the substrate, and may be directed toward the first detector, and a second portion of the emitted source light may be emitted from a second surface of the light source, may pass through a second hole disposed through the substrate, and may be directly directed toward the second detector.

The processor may be further configured to control the light source to emit simultaneously the first portion and the second portion of the source light, from the first surface and the second surface.

The processor may be further configured to drive the optical module, based on a first light pattern, so that the network structure emits a predetermined light pattern.

The first light pattern may be predefined based on either one or both of a type and a characteristic of the object.

The processor may be further configured to control a light intensity of the light source of the optical module disposed at each of the nodes, based on a plurality of light patterns, and drive simultaneously the light source of the optical module disposed at each of the nodes, with the controlled light intensity.

The processor may be further configured to drive sequentially the optical module, based on the first light pattern and then based on a second light pattern different from the first light pattern, and calculate the scattering coefficient and the absorption coefficient, based on the first light and the second light that are detected based on the optical module being driven based on the first light pattern, and based on the first light and the second light that are detected based on the optical module being driven based on the second light pattern.

The processor may be further configured to set the first light pattern and the second light pattern by controlling either one or both of a spatial frequency and a phase of each of the first light pattern and the second light pattern.

The image sensor may be based on spatial frequency domain imaging (SFDI).

The processor may be further configured to generate separately a scattering image and a first absorption image, based on the calculated scattering coefficient and the calculated absorption coefficient.

The processor may be further configured to analyze the component of the object, based on the generated first absorption image.

The processor may be further configured to correct a second absorption image of another component of the object, based on the generated absorption image of the component, wherein the component and the other component affect each other, and analyze the other component, based on the corrected second absorption image.

The component of the object may include any one or any combination of triglycerides, blood glucose, calories, cholesterol, proteins, uric acid, water, and chromophore.

The apparatus may further include an output interface configured to output a result of the analyzed component of the object.

According to embodiments, there is provided a method of analyzing a component of an object, the method including emitting a source light, by a light source, detecting, by a first detector, a first light that is scattered or reflected from the object on which the emitted source light is incident, detecting, by a second detector, a second light that is emitted by the light source but is not incident on the object, calculating, by a processor, a scattering coefficient and an absorption coefficient, based on the detected first light and the detected second light, and analyzing, by the processor, the component of the object, based on the calculated scattering coefficient and the calculated absorption coefficient.

The emitting of the source light may include emitting a first portion of the source light, from a first surface of the light source and toward the object, while simultaneously emitting a second portion of the source light, from a second surface of the light source through a hole disposed through a substrate and toward the second detector.

The method may further include driving, by the processor, the light source disposed at each of nodes of a substrate to form a network structure.

The driving of the light source may include driving the light source, based on a first light pattern, so that the network structure emits a predetermined light pattern.

The driving of the light source may further include controlling a light intensity of the light source disposed at each of the nodes, based on a plurality of light patterns, and driving simultaneously the light source disposed at each of the nodes, with the controlled light intensity.

The driving of the light source may further include driving sequentially the light source, based on the first light pattern and then based on a second light pattern different from the first light pattern.

The calculating of the scattering coefficient and the absorption coefficient may include calculating the scattering coefficient and the absorption coefficient, based on the first light and the second light that are detected based on the light source being driven based on the first light pattern, and based on the first light and the second light that are detected based on the light source being driven based on the second light pattern.

The analyzing of the component of the object may include generating separately a scattering image and an absorption image, based on the calculated scattering coefficient and the calculated absorption coefficient, and analyzing the component of the object, based on the generated absorption image.

The method may further include outputting a result of the analyzed component of the object.

According to embodiments, an image sensor includes a substrate, and an optical module disposed on the substrate. The optical module includes a light source configured to emit a source light, a first detector configured to detect a first light that is emitted from a first surface of the light source and is scattered or reflected from an object, and a second detector configured to detect a second light that is emitted from a second surface of the light source but is not incident on the object.

The optical module may be disposed at each of nodes of the substrate to form a network structure.

The network structure may include any one or any combination of a square shape, a concentric shape, a diamond shape, and a star shape.

The optical module disposed at each of the nodes may be sequentially driven to emit the source light, based on two or more patterns that are set by controlling a spatial frequency of each of the two more patterns.

The light source may be disposed on a first surface of the substrate, and the first detector and the second detector may be disposed on a second surface of the substrate.

The substrate may include a first hole through which the first light reflected or scattered from the object passes, and a second hole through which the second light passes.

The image sensor may further include a light concentrator disposed at a side of the first hole of the substrate, and is configured to direct the first light scattered or reflected from the object toward the first detector.

The light concentrator may include any one or any combination of a waveguide, a condensing lens, a reflection mirror, and a grating.

According to embodiments, an image sensor includes a substrate, and an optical module disposed on the substrate. The optical module includes a light source configured to emit a source light, a first detector configured to detect a first light that is emitted from a first surface of the light source and is scattered or reflected from an object, and a second detector configured to detect a second light that is emitted from a second surface of the light source but is not incident on the object. The image sensor further includes a wavelength controller disposed at one surface of the light source, and configured to control a wavelength band of the source light emitted by the light source.

The optical module may be disposed at each of nodes of the substrate to form a network structure.

The wavelength controller may include a temperature controller configured to control a temperature of the light source to control the wavelength band.

The temperature controller may include either one or both of a resistance heating element and a thermoelement.

The wavelength controller may include a filter configured to pass a predetermined wavelength band of the source light emitted by the light source.

According to embodiments, an image sensor includes a substrate including a plurality of holes, and one or more optical modules disposed on the substrate. Each of the one or more optical modules includes a light source disposed on a first surface of the substrate and disposed over a first side of a first hole among the plurality of holes, a first detector disposed on a second surface of the substrate and disposed over a second hole among the plurality of holes, and a second detector disposed on the second surface of the substrate and disposed over a second side of the first hole. The light source is configured to emit a source light, the first detector is configured to detect a first light that is reflected or scattered from an object on which the emitted source light is incident and that passes through the second hole toward the first detector, and the second detector is configured to detect a second light that is a portion of the emitted source light passing through the first hole toward the second detector.

An apparatus for analyzing a component of the object, includes the image sensor, and a processor configured to control a light intensity of the light source of each of the one or more optical modules, based on a light pattern corresponding to the object.

DETAILED DESCRIPTION

Figure 1:
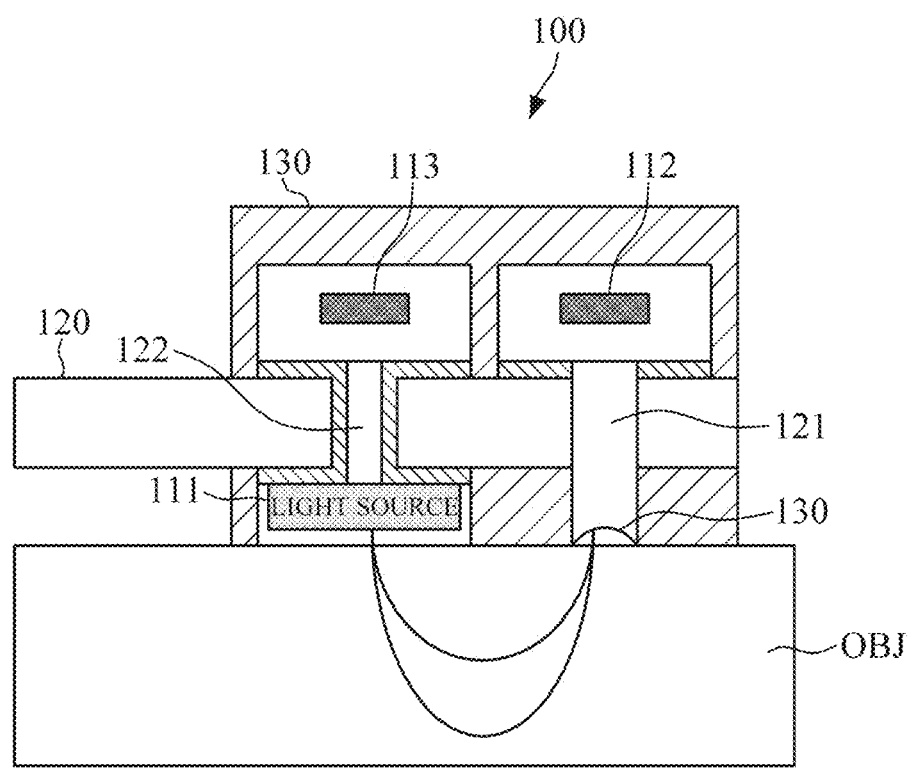
FIGS. 1, 2 and 3 are diagrams schematically illustrating an image sensor according to embodiments of the disclosure.

Details of embodiments are included in the following detailed description and drawings. Advantages and features of the embodiments, and a method of achieving the same will be more clearly understood from the following embodiments described in detail with reference to the accompanying drawings. Throughout the drawings and the detailed description, unless otherwise described, the same drawing reference numerals will be understood to refer to the same elements, features, and structures.

It will be understood that, although the terms first, second, etc. may be used herein to describe various elements, these elements may not be limited by these terms. These terms are only used to distinguish one element from another. Any references to singular may include plural unless expressly stated otherwise. In addition, unless explicitly described to the contrary, an expression such as "comprising" or "including" will be understood to imply the inclusion of stated elements but not the exclusion of any other elements. Also, the terms, such as 'part' or 'module', etc., may be understood as a unit that performs at least one function or operation and that may be embodied as hardware, software, or a combination thereof.

Hereinafter, embodiments of an image sensor will be described in detail with reference to FIGS. 1 to 6.

Figure 2:
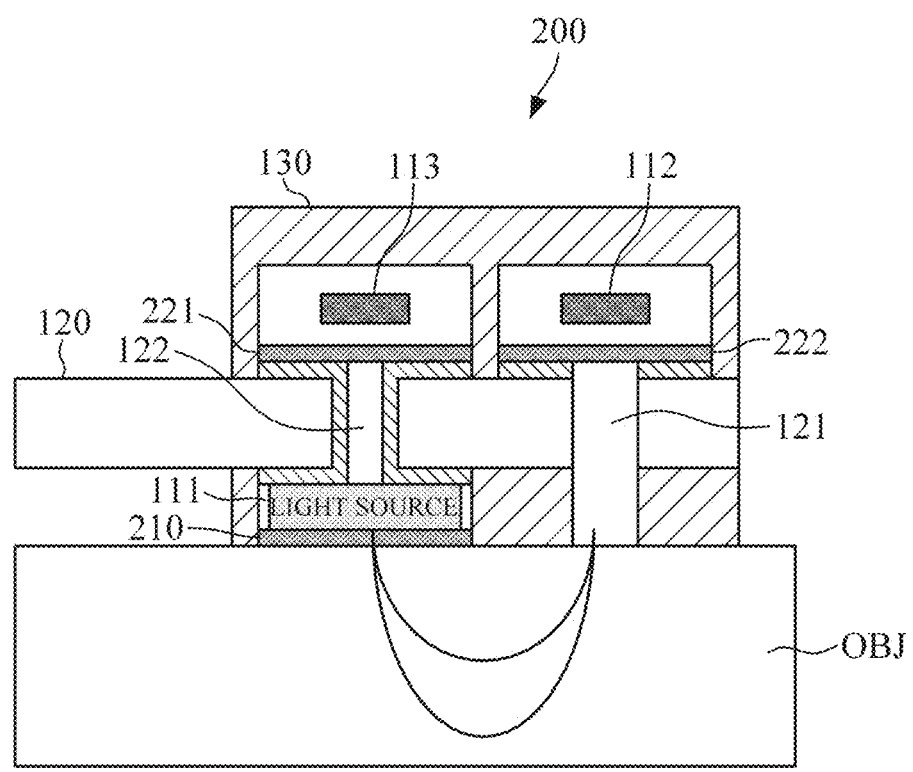
Figure 3:
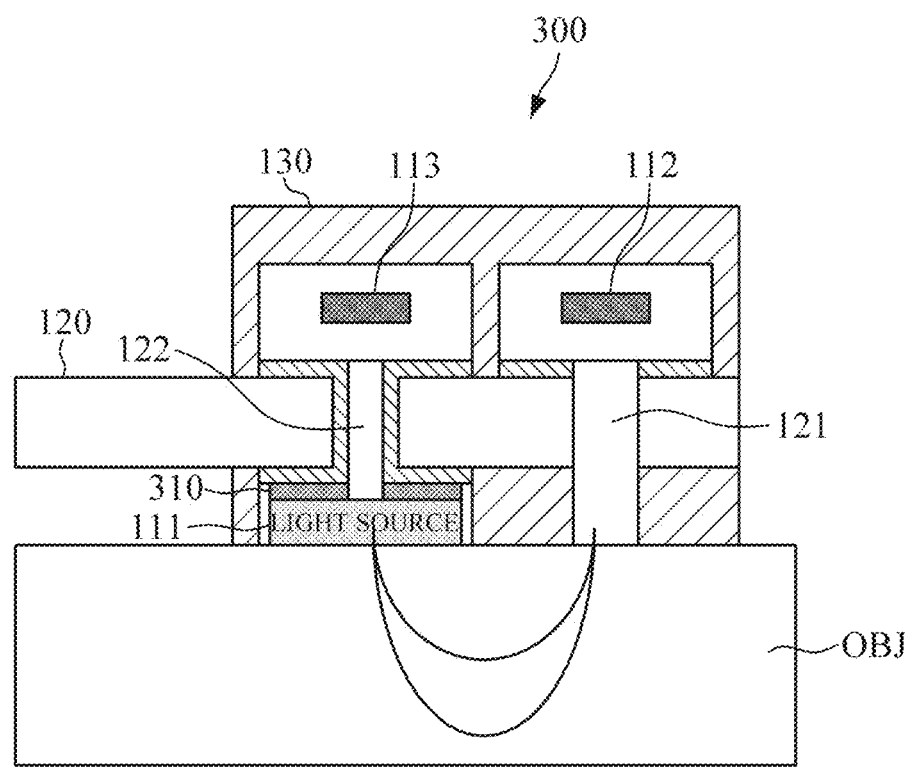
Figure 4:
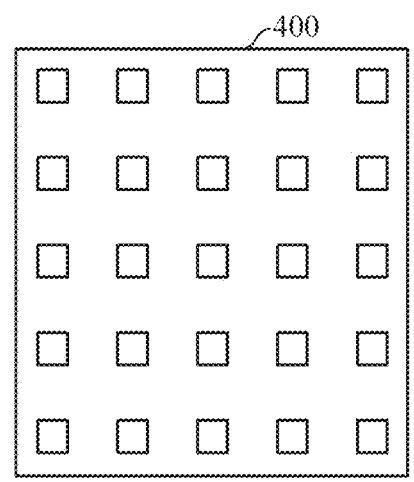
FIG. 4 is a diagram schematically illustrating a network structure of an image sensor according to an embodiment of the disclosure.
Figure 5:
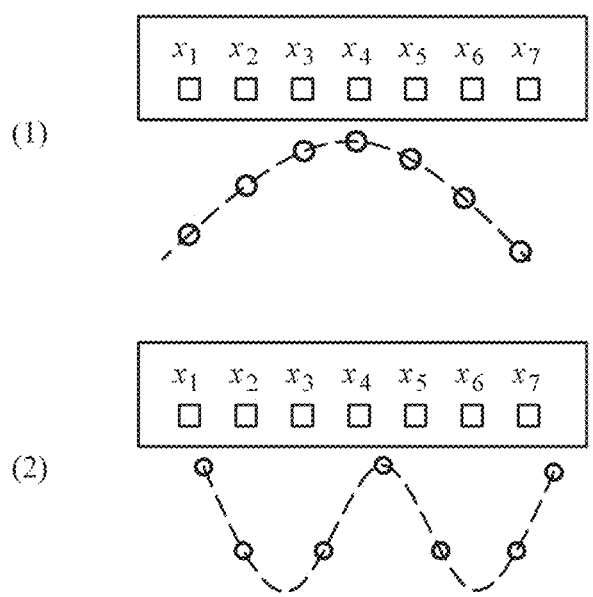
FIG. 5 is a diagram explaining a light pattern of the network structure of the image sensor.
Figure 6:
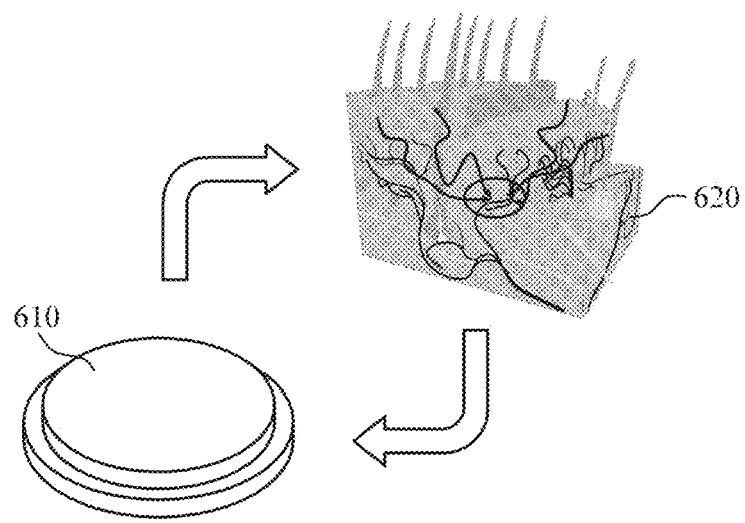
FIG. 6 is a diagram explaining a general method of measuring a reference quantity of light.

FIGS. 1, 2 and 3 are diagrams schematically illustrating an image sensor according to embodiments of the disclosure. FIG. 4 is a diagram schematically illustrating a network structure of an image sensor according to an embodiment of the disclosure. FIG. 5 is a diagram explaining a light pattern of the network structure of the image sensor. FIG. 6 is a diagram explaining a general method of measuring a reference quantity of light.

Referring to FIG. 1, an image sensor 100 according to an embodiment of the disclosure includes a substrate 120 and an optical module disposed on the substrate 120.

The image sensor 100 is formed to have a predetermined network structure, such that optical modules may be disposed one by one at each node of the substrate 120 having a network structure. The pre-defined network structure may have a square shape as illustrated in FIG. 4, but is not limited thereto, and may be pre-defined to have various shapes such as a circular shape, a diamond shape, a concentric shape, a star shape, and the like.

The substrate 120 may be a Printed Circuit Board (PCB). Two holes 121 and 122 are formed on the substrate 120: a first hole 121 is formed on an area of the substrate 120 where a first detector 112 is disposed; and a second hole 122 is formed on an area of the substrate 120 where a second detector 113 is disposed.

The optical module includes a light source 111 configured to emit light, and at least two detectors 112 and 113 configured to detect light emitted by the light source 111. The constituent parts 111, 112, and 113 of the optical module may be formed in a partition wall 130. Each optical module includes a plurality of light sources 111 to emit light of different wavelengths. In this case, each of the light sources may be driven sequentially in a time-division manner.

The light source 111 may include any one or any combination of a light emitting diode (LED), a laser diode, and a fluorescent body.

The first detector 112 may detect a first light that is emitted by the light source 111 and is scattered or reflected from an object OBJ. The second detector 113 may detect a second light that is emitted by the light source 111 but is not incident on the object OBJ. The first detector 112 and the second detector 113 may include any one of a photo diode and a photo transistor (PTr).

The light source 111 may be disposed on a first surface of the substrate 120, and the first detector 112 and the second detector 113 may be disposed on a second surface, e.g., an opposite surface to the first surface, on the substrate 120.

The light source 111 may emit the first light from the first surface toward the object OBJ. The first light, incident on the object OBJ, is absorbed into, or scattered or reflected from, the object OBJ according to characteristics of the object OBJ. The absorbed, scattered, or reflected light passes through the first hole 121 formed at the substrate 120, to enter the first detector 112.

Further, at the same time when emitting the first light from the first surface toward the object OBJ, the light source 111 may emit the second light from the second surface toward the second detector 113. The second light, emitted from the second surface, passes through the second hole 122 formed at the substrate 120, to directly enter the second detector 113.

The image sensor 100 may further include a light concentrator 130 that directs the first light, scattered or reflected from the object OBJ, toward the first detector 112. The light concentrator 130 may include any one or any combination of a waveguide, a condensing lens, a reflection mirror, and a grating.

Referring to FIGS. 2 and 3, image sensors 200 and 300 according to other embodiments of the disclosure may further include a wavelength controller configured to control the wavelength of light emitted by the light source 111, compared to the embodiment of FIG. 1.

Referring to FIG. 2, the wavelength controller may include filters 210, 221, and 222, each of which is configured to pass light in a predetermined wavelength band. The filters 210, 221, and 222 may be, for example, color filters, some of which may not be provided. For example, except for the filter 210 mounted on the first surface of the light source 111, other filters 221 and 222 may not be provided. The filter 210 disposed on the first surface of the light source 111 may be integrally formed or may be formed to be replaceable.

Referring to FIG. 3, the wavelength controller may include a temperature controller 310 configured to control a wavelength band by controlling temperature of the light source 110. The temperature controller 310 may include either one or both of a resistance heating element and a thermoelement, but is not limited thereto. For example, a proper temperature radiating from the light source 111 according to a peak wavelength may be predetermined.

The image sensors 100, 200, and 300 according to embodiments of the disclosure may be disposed so that a plurality of optical modules may form a pre-defined network structure 400, as illustrated in FIG. 4. The image sensors 100, 200, and 300 may be image sensors based on spatial frequency domain.

Referring to FIGS. 4 and 5, the image sensors 100, 200, and 300 may drive light sources of each optical module to have various light patterns by controlling spatial frequency. For example, referring to (1) of FIG. 5, the light sources of each optical module of the image sensors 100, 200, and 300 may be driven in such a manner that according to a light pattern pre-defined to have an upwardly convex parabola shape, a light source $x_4$ of a fourth optical module has the highest light intensity, and the light intensity gradually decreases away from the light source $x_4$ toward both sides thereof. Alternatively, referring to (2) of FIG. 5, the light sources of each optical module of the image sensors 100, 200, and 300 may discretely emit sinusoidal waves by controlling the light intensity of the light sources according to a light pattern pre-defined to have a sinusoidal wave form. Light patterns may be defined according to types and characteristics of an object, and the like, and may be defined to have various shapes such as a concentric shape, a diagonal shape, a diamond shape, and the like.

When the image sensors 100, 200, and 300 according to embodiments of the disclosure analyze components of an object, the first detector 112 measures a quality of light scattered/reflected from the object at the same time when the second detector 113 measures a reference quantity of light, such that image distortion caused by light source drift may be prevented, and the components of the object may be monitored continuously. By contrast, to monitor components of an object, a reference 610 is measured beforehand every time an object, e.g., skin 620, is measured, such that it is not easy to continuously measure components from the skin 620.

Embodiments of an object component analyzing apparatus and object component analyzing method will be described below with reference to FIGS. 7 to 12.

Various embodiments of the object component analyzing apparatus that will be described below may be embedded in various devices such as a mobile wearable device, a smart device, and the like. Examples of the various devices may include, but are not limited to, a wearable device of various types such as a smart watch worn on the wrist, a smart band-type wearable device, a headphone-type wearable device, a hairband-type wearable device, and the like, a mobile device such as a smartphone, a tablet PC, and the like.

Figure 7:
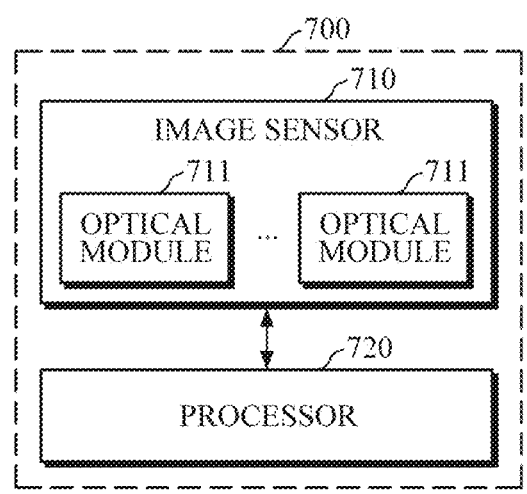
FIG. 7 is a block diagram illustrating an apparatus for analyzing components of an object according to an embodiment of the disclosure.
Figure 8:
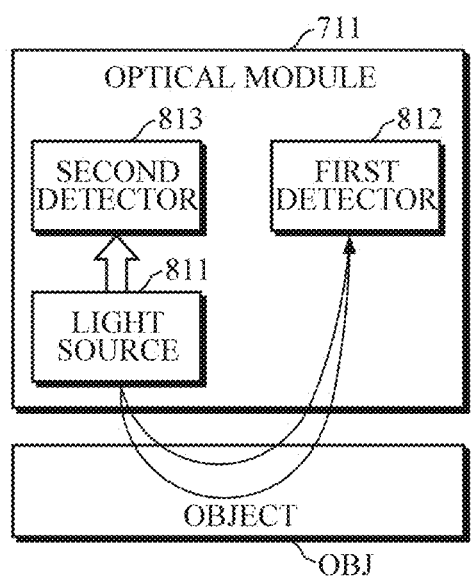
FIG. 8 is a block diagram illustrating an optical module according to the embodiment of FIG. 7.

FIG. 7 is a block diagram illustrating an apparatus for analyzing components of an object according to an embodiment of the disclosure. FIG. 8 is a block diagram illustrating an optical module according to the embodiment of FIG. 7. FIGS. 9A, 9B, 9C and 9D are diagrams explaining an example of obtaining a scattering image and an absorption image. FIGS. 10A, 10B and 10C are diagrams explaining an example of analyzing components of an object.

Referring to FIG. 7, an apparatus 700 for analyzing components of an object includes an image sensor 710 and a processor 720.

The image sensor 710 may be image sensors 100, 200, and 300 described in the above embodiments, and may include a plurality of optical modules 711 as illustrated in FIG. 7. In this case, the image sensor 710 may be an image sensor based on spatial frequency domain.

Referring to FIG. 8, any one of the optical modules 711 may include a light source 811 configured to emit light, and at least two detectors 812 and 813 configured to detect light emitted by the light source 811. Most of the quantity of light emitted by the light source 811 is emitted onto a first surface of the light source 811 that is in contact with an object OBJ, to be incident on the object OBJ, and a portion of the quantity of the emitted light is emitted onto a second surface that is not in contact with the object OBJ.

The first detector 812 may detect a first light, which is scattered or reflected from the object OBJ after being emitted from the first surface of the light source 811 and is incident on the object OBJ. Further, the second detector 813 may directly detect a second light emitted by the light source 811 form the second surface. In this case, the first light, scattered or reflected from the object OBJ, passes through a first hole formed at a substrate of the image sensor 710 to enter the first detector 812; and the second light, emitted by the light source 811 from the second surface, passes through a second hole formed at the substrate of the image sensor 710 to enter the second detector 812.

Referring to FIGS. 7 and 8, the processor 720 may drive each of the light sources 811 of the plurality of optical modules 711 according to a pre-defined light pattern. First, the processor 720 may drive the light source 811 according to a first light pattern. Once the first light and the second light are detected with respect to the first light pattern, and after a predetermined time elapses, the processor 720 may sequentially drive the light source 811 based on a second light pattern that is different from the first light pattern.

Figure 9A:
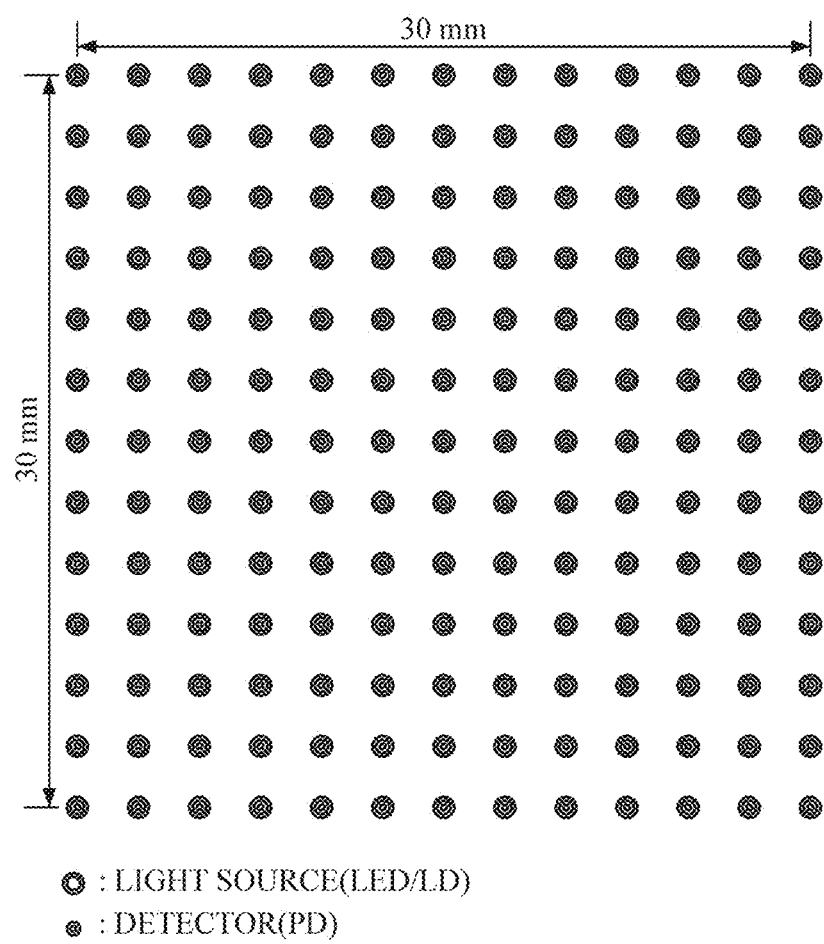
FIGS. 9A, 9B, 9C and 9D are diagrams explaining an example of obtaining a scattering image and an absorption image.
Figure 10A:
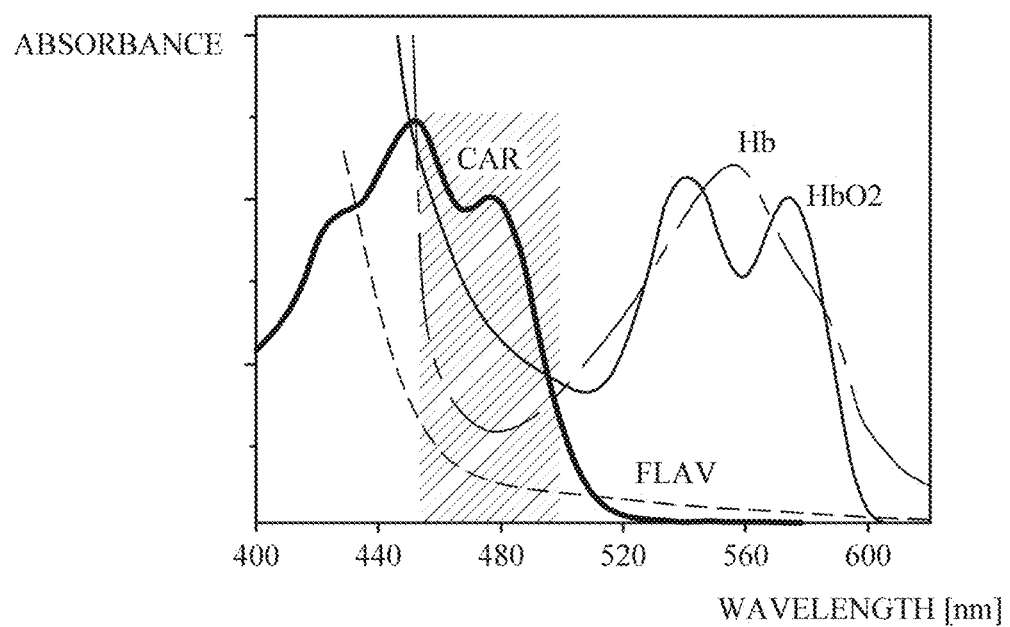
FIGS. 10A, 10B and 10C are diagrams explaining an example of analyzing components of an object.
Figure 10B:
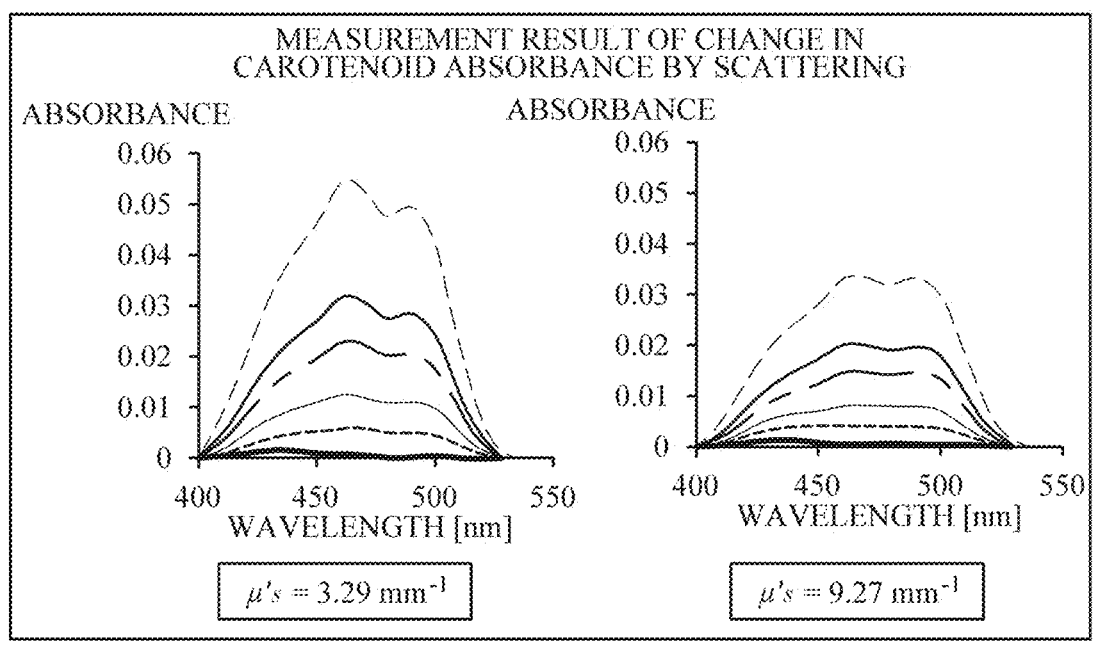
Figure 10C:
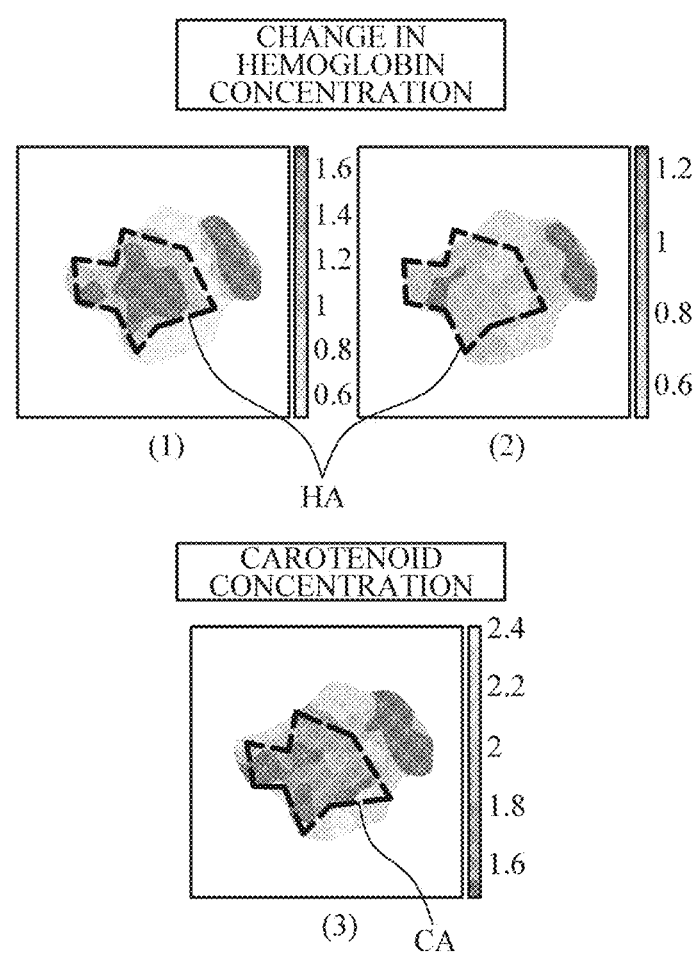

For example, referring to FIG. 9A, the image sensor 710 may be formed to have a square-shaped network structure. The processor 720 may drive each of the optical modules 710 of the image sensor 710, having a network structure, according to a pre-defined light pattern. In this case, the light pattern may be set by controlling either one or both of spatial frequency and phase.

Figure 9B:
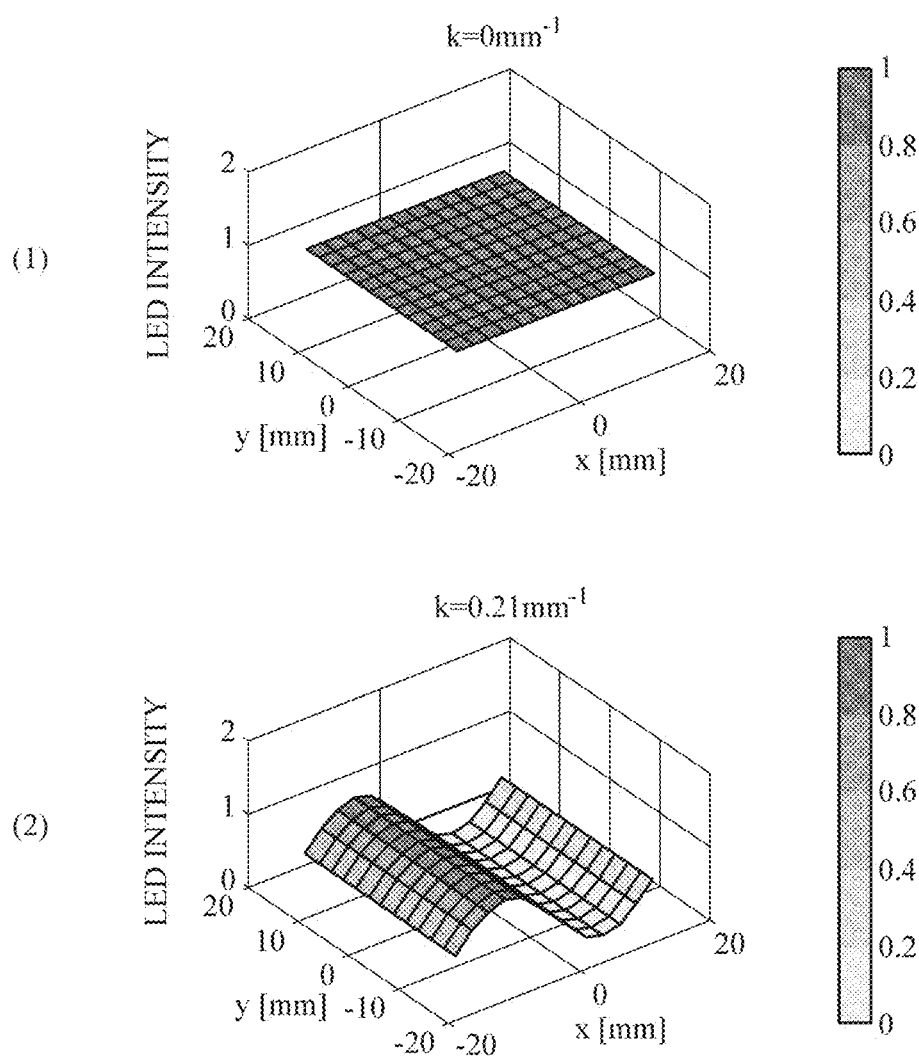

Referring to FIG. 9B, (1) illustrates an example of driving all the light sources 811 with the same light intensity according to a first light pattern in which spatial frequency k is set at 0 mm$^{-1}$; and (2) illustrates an example of driving the light sources 811 by controlling the light intensity in the form of sinusoidal waves according to a second light pattern in which spatial frequency k is set at 0.21 mm$^{-1}$. In this case, phase offset is set to 0°, 120°, and 240° for each spatial frequency, such that light pattern modulations may be provided six times in total.

Figure 9C:
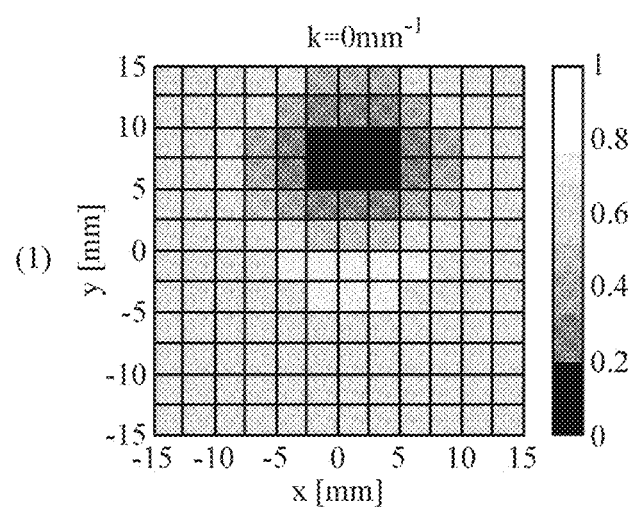
Figure 9C:
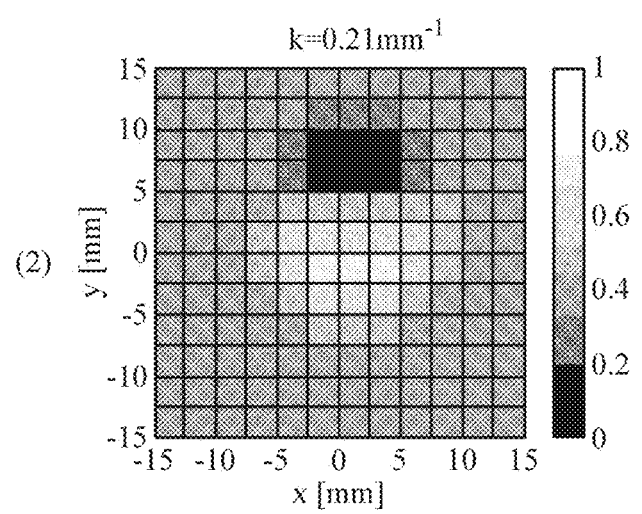

Referring to FIG. 9C, (1) illustrates an image obtained by driving the light sources 811 according to a first light pattern in which the spatial frequency k is set at 0 mm$^{-1}$; and (2) illustrates an image obtained by driving the light sources 811 according to a second light pattern in which the spatial frequency k is set at 0.21 mm$^{-1}$. As illustrated in (1) and (2) of FIG. 9, an image obtained at a spatial frequency includes a combination of scattering and absorption characteristics, such that accuracy of analysis may be reduced when a component is analyzed using absorption characteristics.

Referring again to FIGS. 7 and 8, the processor 720 may calculate a scattering coefficient and an absorption coefficient, based on the first light and the second light detected by the first detector 812 and the second detector 813 of each optical module 711.

For example, the processor 720 may calculate scattering reflectance based on the quantity of the first light and the quantity of the second light that are detected by the first detector 812 and the second detector 813 with respect to two or more light patterns. In this case, the processor 720 may calculate a first scattering reflectance based on a ratio of the first quantity of light to the second quantity of light, which are measured by the first detector 812 and the second detector 813 according to the first light pattern. Further, the processor 720 may calculate a second scattering reflectance based on a ratio of the first quantity of light to the second quantity of light that are detected according to the second light pattern.

The processor 720 may calculate the scattering coefficient $\mu'_s$ and the absorption coefficient $\mu_a$ by substituting, in the following Equation 1, each scattering reflectance and each spatial frequency that are calculated with respect to each light pattern. Alternatively, the processor 720 may calculate the scattering coefficient μ'$_s$ and the absorption coefficient μ$_a$ by using a lookup table representing a correlation between the scattering coefficient μ'$_s$ and the absorption coefficient μ$_a$.

$$R_d(k, \mu_a, \mu'_s) = \frac{3A\mu'_s}{((3\mu_a(\mu_a + \mu'_s) + k^2)^{1/2} + \mu_a + \mu'_s)} \quad \text{[Equation 1]}$$
$$((3\mu_a(\mu_a + \mu'_s) + k^2)^{1/2} + 3A(\mu_a + \mu'_s))$$

Herein, $R_d$ (k, μ$_a$, μ'$_s$) denotes the scattering reflectance at each spatial frequency k, and A denotes a pre-defined constant value. Generally, as the spatial frequency is increased, the scattering reflectance is reduced. In this case, the relationship between the scattering reflectance and the spatial frequency has characteristics of a low pass filter.

Further, the processor 720 may separately generate a scattering image and an absorption image by using the calculated scattering coefficient μ'$_s$ and absorption coefficient μ$_a$, and may analyze components of an object by using each of the generated images. In this case, the components of an object may include one or more of triglycerides, blood glucose, calories, cholesterol, proteins, uric acid, water, and chromophore. The chromophore may include hemoglobin, carotenoid, melanin, antioxidant, water, melanoma, and the like, but is not limited thereto.

Figure 9D:
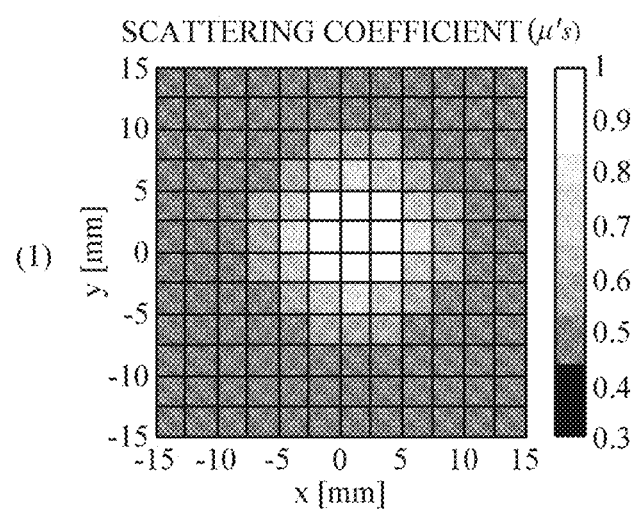
Figure 9D:
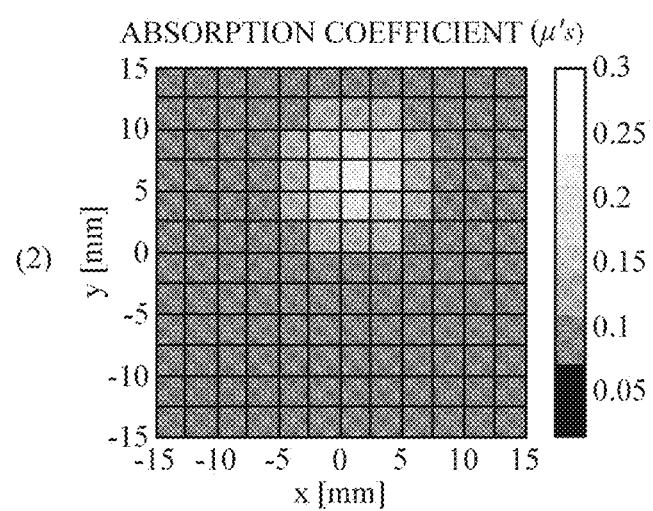

Referring to FIG. 9D, the processor 720 may separately generate (1) a scattering image according to the scattering coefficient μ'$_s$ and (2) an absorption image according to the absorption coefficient μ$_a$. In this case, unlike FIG. 9C, the processor 720 may obtain the absorption image according to an absorption effect from which characteristics of the scattering coefficient are removed, such that components of an object may be analyzed more accurately.

Referring again to FIG. 7, the processor 720 may correct an absorption image of a second component (e.g., carotenoid) based on an absorption image of a first component (e.g., hemoglobin) of an object among two or more components that affect each other, and may analyze the second component based on the corrected absorption image.

For example, referring to FIGS. 10A to 10C, the processor 720 may analyze a carotenoid component of an object. Referring to FIG. 10A, measuring a carotenoid concentration is generally affected by scattering and absorption effects of components such as hemoglobin, melanin, and the like. As described above, in the case in which an undesired tissue component is present in the path of measured light, the absorption and scattering characteristics are affected by the tissue component, thereby causing a significant error in a measured value. FIG. 10B is a diagram illustrating a measurement result of a change in absorbance of carotenoid according to scattering characteristics, in which it can be seen that absorbance, measured at a point where a scattering coefficient is high, is relatively lower than absorbance measured at a point where a scattering coefficient is low.

Referring to FIG. 10C, to analyze, for example, the carotenoid component, the processor 720 may monitor an area HA, which is affected by a component other than the carotenoid component, for example, a change in hemoglobin concentration, based on (1) a 2D absorption image obtained at a first time and (2) a 2D absorption image obtained at a second time. The processor 720 may improve reliability of analysis of the carotenoid component by correcting an area CA, which is affected by the hemoglobin concentration, in (3) a 2D absorption image obtained at a third time based on a monitoring result of (2).

Referring again to FIG. 7, upon calculating the scattering coefficient and the absorption coefficient as described above, the processor 720 may measure a concentration of a component of an object by using either one or both of the scattering coefficient and the absorption coefficient. For example, the processor 720 may measure the concentration of a component of an object by using a component measurement equation, which represents a correlation between the scattering coefficient and a component concentration or between the absorption coefficient and a component concentration, as represented by the following Equation 2. The following Equation 2 is in the form of a linear function, but is not limited thereto, and may be defined in the form of a non-linear function, or a matching table.

$$y = ax + b \quad \text{[Equation 2]}$$

Herein, y denotes the concentration of a component, x denotes the scattering coefficient or the absorption coefficient, and a and b denote predefined constant values.

Figure 11:
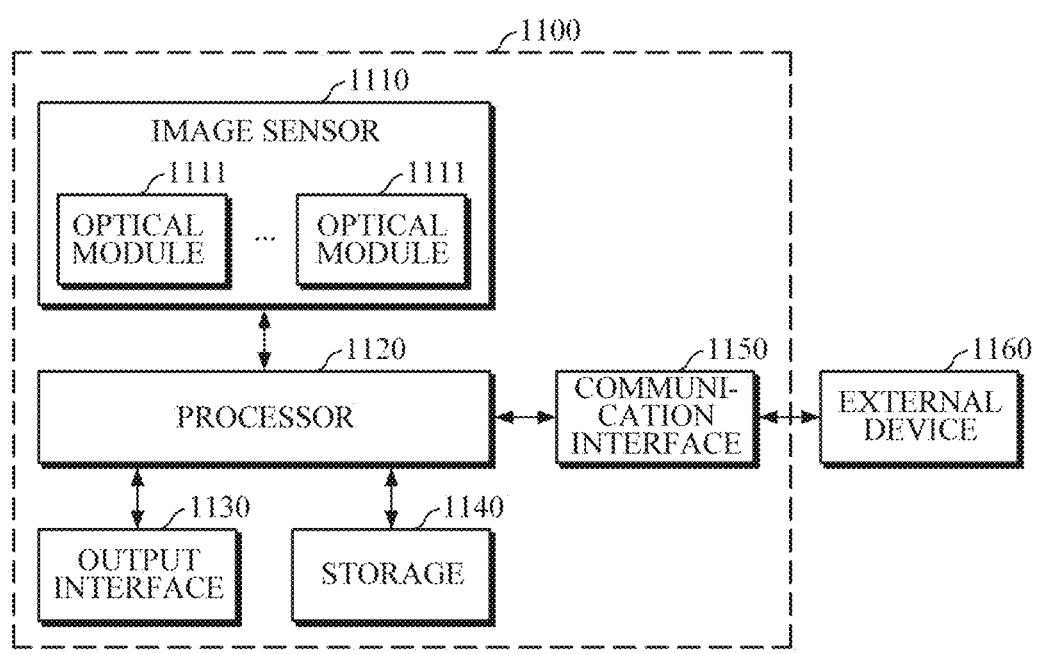
FIG. 11 is a block diagram illustrating an apparatus for analyzing components of an object according to another embodiment of the disclosure.

FIG. 11 is a block diagram illustrating an apparatus for analyzing components of an object according to another embodiment of the disclosure.

Referring to FIG. 11, an apparatus 1100 for analyzing components of an object (hereinafter referred to as an object component analyzing apparatus) includes an image sensor 1110, a processor 1120, an output interface 1130, a storage 1140, and a communication interface 1150. Parts with the same name as those of the component analyzing apparatus 700 of FIG. 7 will be briefly described below.

The image sensor 1110 is formed to have a predefined network structure, of which each node includes respective optical modules 1111. Each optical module 1111 may include a light source, a first detector for measuring the quantity of light scattered/reflected from an object, and a second detector for measuring a reference quantity of light at the same time as measurement of the first detector.

The processor 1120 may sequentially drive each optical module 1111 of the image sensor 1110 according to predefined two or more light patterns. The processor 1120 may drive a light source by controlling a light intensity or a phase of each light source defined according to a light pattern.

The processor 1120 may calculate each scattering reflectance based on a quantity of light scattered/reflected from an object and a reference quantity of light that are detected according to two or more light patterns, and may calculate a scattering coefficient and an absorption coefficient based on each scattering reflectance and each spatial frequency. Further, the processor 1120 may separately generate a scattering image and an absorption image based on the calculated scattering coefficient and absorption coefficient.

The processor 1120 may analyze components of an object more accurately based on an absorption image, from which scattering characteristics are removed. In addition, the processor 1120 may obtain a component concentration of an object based on the absorption coefficient or the scattering coefficient. The processor 1120 may monitor a user's health condition based on the component concentration of an object.

The output interface 1130 may output a processing result of the processor 11120 to a user. For example, the output interface 1130 may visually display information on a light pattern, which is currently in use, by using, for example, the same method as FIG. 9B. Further, the output interface 1130 may visually display the scattering image and the absorption image as illustrated in FIG. 9D. In addition, the output interface 1130 may visually or non-visually provide information on a measured component concentration of an object to a user. Besides, the output interface 1130 may output information on a monitored health condition of a user. In this case, the output interface 1130 may provide the information to a user by changing color of a component concentration value output on a display or through tactile sensation or vibration by using a haptic module.

The storage 1140 may store various types of reference information. For example, the reference information may include light pattern information, a function equation for measuring a component of a user, and user information including a user's age, gender, health condition, and the like. Further, the storage 1140 may store the processing result of the processor 1120. For example, the storage 1140 may store the calculated scattering coefficient and absorption coefficient, the generated scattering image and absorption image, and component concentration information of an object, and the like.

In this case, the storage 1140 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like.

The communication interface 1150 may communicate with an external device 1160 to receive various types of reference information from the external device 1160. The received reference information may be stored in the storage 1130. Further, the communication interface 1150 may transmit the calculated scattering coefficient and absorption coefficient, the generated scattering image and absorption image, and an analysis result of components of an object, and the like to the external device 1160. In this case, examples of the external device 1160 may include an information processing apparatus such as a smartphone, a tablet PC, a desktop computer, and the like, and a component measuring apparatus for measuring a component of an object in an invasive manner.

In this case, the communication interface 1150 may perform communication by using Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, 3G communication, 4G communication, 5G communication, and the like. However, this is an example and is not intended to be limiting.

Figure 12:
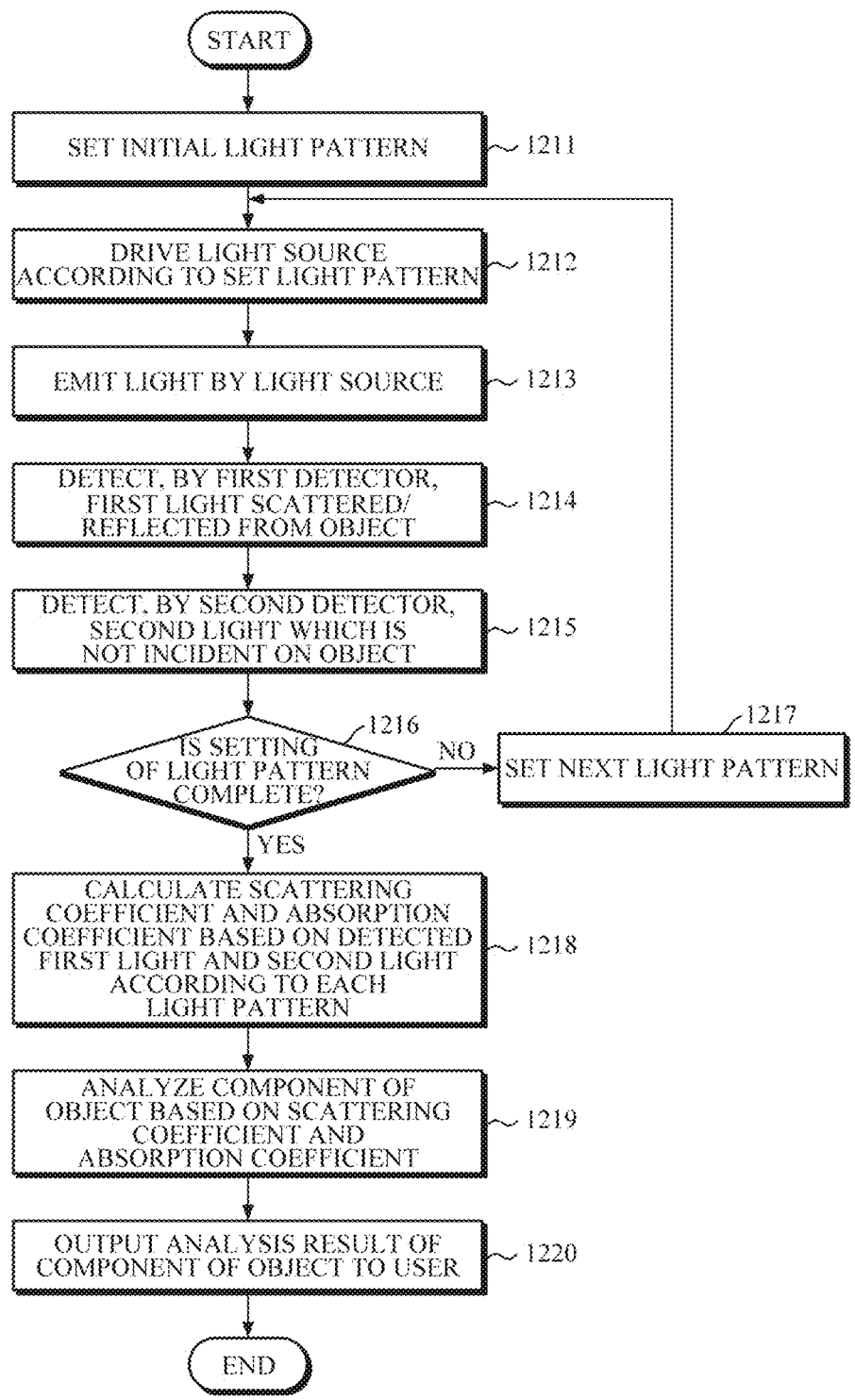
FIG. 12 is a flowchart illustrating a method of analyzing components of an object according to embodiments of the disclosure.

FIG. 12 is a flowchart illustrating a method of analyzing components of an object according to embodiments of the disclosure.

The method of analyzing components of an object (hereinafter referred to as an object component analyzing method) of FIG. 12 may be an example of an object component analyzing method performed by the object component analyzing apparatuses 700 and 1100 described above with reference to the embodiments of FIGS. 7 to 11.

Referring to FIG. 12, upon receiving a request for analyzing a component of an object, the object component analyzing apparatus may set an initial light pattern in 1211.

In this case, the request for analyzing a component of an object may be input by a user. However, the request is not limited thereto, and may be preset to be automatically input into the object component analyzing apparatus repeatedly at predetermined intervals. Further, the light pattern may be defined as two or more different patterns to discretely emit sinusoidal waves by controlling spatial frequency and phase. Further, an order of setting each light pattern may be predefined.

Then, the object component analyzing apparatus may drive a light source according to a set light pattern in 1212, and each light source may emit light in 1213.

Subsequently, the first detector may detect a first light scattered/reflected from an object in 1214. After being emitted by the light source toward the object, light is incident on the object, and is scattered or reflected according to tissue components in the object, to enter the first detector.

Further, at the same time, the second detector may detect a second light that is emitted by the light source but is not incident on the object in 1215. Most of the light emitted by the light source is emitted toward the object, and some of the light is emitted toward the second detector.

Next, once the first light and the second light are detected in 1214 and 1215 respectively according to the set light patterns, the object component analyzing apparatus confirms whether there is a next light pattern to be set in 1216; and in the case in which there is a next light pattern to be set, the object component analyzing apparatus sets the next light pattern in 1217, and may perform again the operation 1212 and the operations subsequent thereto.

Then, once the first light and the second light are detected in 1214 and 1215 respectively according to two or more different light patterns, the object component analyzing apparatus may calculate the scattering coefficient and the absorption coefficient based on the first light and the second light in 1218. For example, the object component analyzing apparatus may calculate first scattering reflectance based on a ratio between a first quantity of light and a second quantity of light that are detected according to the first light pattern among the two or more light patterns, and may calculate second scattering reflectance based on a ratio between a first quantity of light and a second quantity of light that are detected according to a second light pattern. Further, the object component analyzing apparatus may calculate a scattering coefficient and an absorption coefficient based on the spatial frequency according to the first scattering reflectance and the first light pattern, and the spatial frequency according to the second scattering reflectance and the second light pattern.

Subsequently, the object component analyzing apparatus may analyze a component of an object based on the calculated scattering coefficient and absorption coefficient in 1219. For example, the object component analyzing apparatus may separately generate a scattering image and an absorption image based on the scattering coefficient and the absorption coefficient. The object component analyzing apparatus may correct an absorption image of a component to be measured based on an absorption image of other components affecting the object component to be analyzed, and may analyze the object component by analyzing the corrected image. Alternatively, upon calculating the scattering coefficient and the absorption coefficient, the object component analyzing apparatus may measure a component concentration of the object by using either one or both of the scattering coefficient and the absorption coefficient. For example, the object component analyzing apparatus may measure a component concentration of the object by using a component measurement equation, which represents a correlation between the absorption coefficient and the component concentration.

Next, the object component analyzing apparatus may output an analysis result of components of an object to a user in 1220. For example, the object component analyzing apparatus may visually or non-visually provide concentration information of an object component to a user. Further, the object component analyzing apparatus may output information on the monitored health condition of a user.

Embodiments can be realized as a computer-readable code written on a computer-readable recording medium. The computer-readable recording medium may be any type of recording device in which data is stored in a computer-readable manner.

Examples of the computer-readable recording medium include a ROM, a RAM, a CD-ROM, a magnetic tape, a floppy disc, an optical data storage, and a carrier wave (e.g., data transmission through the Internet). The computer-readable recording medium can be distributed over a plurality of computer systems connected to a network so that a computer-readable code is written thereto and executed therefrom in a decentralized manner. Functional programs, codes, and code segments for realizing embodiments can be easily deduced by one of ordinary skill in the art.

Embodiments have been described herein. However, it will be obvious to those skilled in the art that various changes and modifications can be made without changing technical ideas and features of the disclosure. Thus, it is clear that the above-described embodiments are illustrative in all aspects and are not intended to limit the disclosure.

What is claimed is:

1. An apparatus for analyzing a component of an object, the apparatus comprising:
   an image sensor comprising an optical module, wherein the optical module comprises:
     a light source configured to emit a source light;
     a first detector configured to detect a first light that is scattered or reflected from the object on which the emitted source light is incident; and
     a second detector configured to detect a second light that is emitted by the light source but is not incident on the object; and
   a processor configured to:
     calculate a scattering coefficient and an absorption coefficient, based on the detected first light and the detected second light; and
     analyze the component of the object, based on the calculated scattering coefficient and the calculated absorption coefficient,
   wherein the image sensor further comprises a substrate on which the optical module is disposed at each of nodes to form a network structure,
   wherein a first portion of the emitted source light is emitted from a first surface of the light source, is incident on the object, is scattered or reflected from the object, passes through a first hole disposed through the substrate, and is directed toward the first detector, and
   wherein a second portion of the emitted source light is emitted from a second surface of the light source, passes through a second hole disposed through the substrate, and is directly directed toward the second detector.

2. The apparatus of claim 1, wherein the processor is further configured to control the light source to emit simultaneously the first portion and the second portion of the source light, from the first surface and the second surface.

3. An image sensor comprising:
   a substrate; and
   an optical module disposed on the substrate, wherein the optical module comprises:
     a light source configured to emit a source light;
     a first detector configured to detect a first light that is emitted from a first surface of the light source and is scattered or reflected from an object; and
     a second detector configured to detect a second light that is emitted from a second surface of the light source but is not incident on the object,
   wherein the light source is disposed on a first surface of the substrate,
   wherein the first detector and the second detector are disposed on a second surface of the substrate, and
   wherein the substrate comprises:
     a first hole through which the first light reflected or scattered from the object passes; and
     a second hole through which the second light passes.

4. The image sensor of claim 3, further comprising a light concentrator disposed at a side of the first hole of the substrate, and is configured to direct the first light scattered or reflected from the object toward the first detector.

5. The image sensor of claim 4, wherein the light concentrator comprises any one or any combination of a waveguide, a condensing lens, a reflection mirror, and a grating.

6. An image sensor comprising:
   a substrate comprising a plurality of holes;
   one or more optical modules disposed on the substrate, wherein each of the one or more optical modules comprises:
     a light source disposed on a first surface of the substrate and disposed over a first side of a first hole among the plurality of holes;
     a first detector disposed on a second surface of the substrate and disposed over a second hole among the plurality of holes; and
     a second detector disposed on the second surface of the substrate and disposed over a second side of the first hole,
   wherein the light source is configured to emit a source light,
   wherein the first detector is configured to detect a first light that is reflected or scattered from an object on which the emitted source light is incident and that passes through the second hole toward the first detector, and
   wherein the second detector is configured to detect a second light that is a portion of the emitted source light passing through the first hole toward the second detector.

7. An apparatus for analyzing a component of the object, the apparatus comprising:
   the image sensor of claim 6; and
   a processor configured to control a light intensity of the light source of each of the one or more optical modules, based on a light pattern corresponding to the object.

* * * * *